US010687988B2

(12) United States Patent
Morimoto et al.

(10) Patent No.: US 10,687,988 B2
(45) Date of Patent: Jun. 23, 2020

(54) ABSORBENT ARTICLE HAVING CHARACTERISTIC WAIST ENDS

(71) Applicant: The Procter & Gamble Company, Cincinnati, OH (US)

(72) Inventors: Koichi Morimoto, Beijing (CN); Katsuhiro Yonemura, Kobe (JP); Gary Dean LaVon, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 541 days.

(21) Appl. No.: 13/893,788

(22) Filed: May 14, 2013

(65) Prior Publication Data

US 2013/0317471 A1  Nov. 28, 2013

(30) Foreign Application Priority Data

May 15, 2012 (CN) .............................. 2012 1 075490
Apr. 25, 2013 (CN) .............................. 2013 1 074721

(51) Int. Cl.
*A61F 13/49* (2006.01)
*A61F 13/84* (2006.01)
*A61F 13/496* (2006.01)

(52) U.S. Cl.
CPC ...... *A61F 13/49012* (2013.01); *A61F 13/496* (2013.01); *A61F 13/49011* (2013.01);
(Continued)

(58) Field of Classification Search
CPC .. A61F 13/49011; A61F 13/496; A61F 13/84; A61F 13/49012; A61F 13/49061; A61F 2013/8497
(Continued)

(56) References Cited

U.S. PATENT DOCUMENTS

| 364,029 A | 5/1887 | Macnab |
| 429,891 A | 6/1890 | Crowell |

(Continued)

FOREIGN PATENT DOCUMENTS

| DE | G93 17 680.5 | 4/1995 |
| EP | 397110 B2 | 3/1990 |

(Continued)

OTHER PUBLICATIONS

"Pampers Ultra Trainers" package, Size 3 from Finneytown Kroger's dated Oct. 3, 1998.

(Continued)

*Primary Examiner* — Andrew J Mensh
(74) *Attorney, Agent, or Firm* — Charles R. Matson; Richard L. Alexander (57) ABSTRACT

The present disclosure is directed to an absorbent article that may comprise a main body graphic zone. A front belt portion and a back belt portion may each have a waist end region adjacent a waist opening, wherein front and back waist panels of an absorbent main body do not overlap with front or back waist end regions. The front and back belt portions may each have a leg end region adjacent the proximal edges. Left and right side panels of the front and back belt portions may each have a tummy belt region between the waist end region and the leg end region. And, the waist end region may have an opacity of at least 15 points greater than that of the tummy belt region.

23 Claims, 4 Drawing Sheets

(52) U.S. Cl.
CPC ........ *A61F 13/49061* (2013.01); *A61F 13/84* (2013.01); *A61F 2013/8497* (2013.01)

(58) Field of Classification Search
USPC ..................................................... 604/385.3
See application file for complete search history.

(56) References Cited

U.S. PATENT DOCUMENTS

| | | |
|---|---|---|
| 1,639,218 A | 8/1927 | Ebersol |
| 2,075,189 A | 3/1937 | Galligan et al. |
| 2,111,613 A | 3/1938 | Bulford |
| 2,175,051 A | 10/1939 | Bromley |
| 2,378,444 A | 6/1945 | Smith et al. |
| 2,404,350 A | 7/1946 | Carlsen et al. |
| 2,504,021 A | 4/1950 | Heinrich |
| 2,743,206 A | 4/1956 | Verduin |
| 3,306,194 A | 2/1967 | Cutri |
| 3,306,196 A | 2/1967 | Cutri |
| 3,442,211 A | 5/1969 | Beacham |
| 3,518,940 A | 7/1970 | Stroud et al. |
| 3,675,654 A | 7/1972 | Baker |
| 3,759,261 A | 9/1973 | Wang |
| 3,848,594 A | 11/1974 | Buell |
| 3,860,003 A | 1/1975 | Buell |
| 3,881,491 A | 5/1975 | Whyte |
| 3,911,173 A | 10/1975 | Sprague, Jr. |
| 3,921,232 A | 11/1975 | Whyte |
| 3,929,135 A | 12/1975 | Thompson |
| 3,978,789 A | 9/1976 | Fennekels et al. |
| 4,020,153 A | 4/1977 | Rowsell et al. |
| 4,022,210 A | 5/1977 | Glassman |
| 4,022,211 A | 5/1977 | Timmons |
| 4,032,661 A | 6/1977 | Rowsell et al. |
| 4,033,994 A | 7/1977 | Watson et al. |
| 4,034,109 A | 7/1977 | Rowsell et al. |
| 4,063,505 A | 12/1977 | Sasamoto et al. |
| 4,069,822 A | 1/1978 | Buell |
| 4,070,449 A | 1/1978 | Rowsell et al. |
| 4,070,496 A | 1/1978 | Rowsell et al. |
| 4,078,568 A | 3/1978 | Etes et al. |
| 4,081,301 A | 3/1978 | Buell |
| 4,089,765 A | 5/1978 | Dudley |
| 4,107,364 A | 8/1978 | Sisson |
| 4,140,115 A | 2/1979 | Schonfeld |
| 4,147,580 A | 4/1979 | Buell |
| 4,150,052 A | 4/1979 | Watson et al. |
| 4,153,679 A | 5/1979 | Rowsell et al. |
| 4,178,459 A | 12/1979 | Watson et al. |
| 4,192,311 A | 3/1980 | Felfoldi |
| 4,192,785 A | 3/1980 | Chen et al. |
| 4,193,936 A | 3/1980 | Watson et al. |
| 4,205,679 A | 6/1980 | Repke |
| 4,209,563 A | 6/1980 | Sisson |
| 4,218,973 A | 8/1980 | Bouffard et al. |
| 4,226,988 A | 10/1980 | Watson et al. |
| 4,231,369 A | 11/1980 | Sorensen et al. |
| 4,231,370 A | 11/1980 | Mroz |
| 4,232,076 A | 11/1980 | Stetson et al. |
| 4,249,532 A | 2/1981 | Polansky et al. |
| 4,281,598 A | 8/1981 | Rump |
| 4,284,454 A | 8/1981 | Joa |
| 4,289,794 A | 9/1981 | Kleiner et al. |
| 4,292,916 A | 10/1981 | Bradley et al. |
| 4,296,093 A | 10/1981 | Rowsell et al. |
| 4,296,255 A | 10/1981 | Roswell et al. |
| 4,300,967 A | 11/1981 | Sigl |
| 4,324,246 A | 4/1982 | Mullane et al. |
| 4,327,731 A | 5/1982 | Powell |
| 4,328,181 A | 5/1982 | Anders et al. |
| 4,340,212 A | 7/1982 | Simson |
| 4,342,314 A | 8/1982 | Radel et al. |
| 4,393,080 A | 7/1983 | Pawelchak et al. |
| 4,459,425 A | 7/1984 | Amano et al. |
| 4,463,045 A | 7/1984 | Ahr et al. |
| 4,501,072 A | 2/1985 | Jacobi, Jr. et al. |
| 4,505,976 A | 3/1985 | Doehnert et al. |
| 4,507,121 A | 3/1985 | Leung |
| 4,515,595 A | 5/1985 | Kievit et al. |
| 4,551,490 A | 11/1985 | Doyle et al. |
| 4,573,986 A | 3/1986 | Minetola et al. |
| 4,574,022 A | 3/1986 | Johnson |
| 4,585,450 A | 4/1986 | Rosch et al. |
| D284,036 S | 6/1986 | Birring |
| 4,593,053 A | 6/1986 | Jevne et al. |
| 4,609,518 A | 9/1986 | Curro et al. |
| 4,609,587 A | 9/1986 | Giordano et al. |
| 4,610,678 A | 9/1986 | Weisman et al. |
| 4,629,643 A | 12/1986 | Curro et al. |
| 4,636,207 A | 1/1987 | Buell |
| 4,662,875 A | 5/1987 | Hirotsu et al. |
| 4,663,220 A | 5/1987 | Wisneski et al. |
| 4,673,402 A | 6/1987 | Weisman et al. |
| 4,695,278 A | 9/1987 | Lawson |
| 4,699,146 A | 10/1987 | Sieverding |
| 4,699,622 A | 10/1987 | Toussant et al. |
| 4,704,115 A | 11/1987 | Buell |
| 4,704,116 A | 11/1987 | Enloe |
| 4,705,513 A | 11/1987 | Sheldon |
| 4,710,189 A | 12/1987 | Lash |
| 4,720,415 A | 1/1988 | Vander Wielen et al. |
| 4,738,257 A | 4/1988 | Meyer et al. |
| 4,743,241 A | 5/1988 | Igaue |
| 4,785,996 A | 11/1988 | Ziecker et al. |
| 4,795,454 A | 1/1989 | Dragoo |
| 4,808,178 A | 2/1989 | Aziz et al. |
| 4,812,053 A | 3/1989 | Bhattacharjee |
| 4,816,025 A | 3/1989 | Foreman |
| 4,824,503 A | 4/1989 | Wilen |
| 4,834,735 A | 5/1989 | Alemany et al. |
| 4,834,741 A | 5/1989 | Sabee |
| 4,842,666 A | 6/1989 | Werenicz |
| 4,846,815 A | 7/1989 | Scripps |
| 4,854,984 A | 8/1989 | Ball |
| 4,888,231 A | 12/1989 | Angstadt |
| 4,892,536 A | 1/1990 | Desmarais et al. |
| 4,894,060 A | 1/1990 | Nestegard |
| 4,903,254 A | 2/1990 | Haas |
| 4,909,803 A | 3/1990 | Aziz et al. |
| 4,931,051 A | 6/1990 | Castello |
| 4,940,464 A | 7/1990 | Van Gompel et al. |
| 4,946,527 A | 8/1990 | Battrell |
| D310,880 S | 9/1990 | Majewski |
| 4,963,140 A | 10/1990 | Robertson et al. |
| 4,965,122 A | 10/1990 | Morman |
| 4,967,660 A | 11/1990 | Yamanari et al. |
| 4,968,312 A | 11/1990 | Khan |
| 4,977,011 A | 12/1990 | Smith |
| 4,980,705 A | 12/1990 | Akutsu et al. |
| 4,981,747 A | 1/1991 | Morman |
| 4,987,849 A | 1/1991 | Sherman |
| 4,990,147 A | 2/1991 | Freeland |
| 5,006,394 A | 4/1991 | Baird |
| 5,026,364 A | 6/1991 | Robertson |
| 5,037,416 A | 8/1991 | Allen et al. |
| 5,045,283 A | 9/1991 | Patel |
| 5,053,339 A | 10/1991 | Patel |
| 5,058,088 A | 10/1991 | Haas et al. |
| 5,062,840 A | 11/1991 | Holt et al. |
| 5,064,421 A | 11/1991 | Tracy |
| 5,086,700 A | 2/1992 | Van Den Berg |
| 5,092,861 A | 3/1992 | Nomura et al. |
| D325,256 S | 4/1992 | Landsman et al. |
| 5,114,781 A | 5/1992 | Morman |
| 5,116,662 A | 5/1992 | Morman |
| 5,124,188 A | 6/1992 | Roe et al. |
| 5,133,707 A | 7/1992 | Rogers et al. |
| 5,137,537 A | 8/1992 | Herron et al. |
| 5,143,679 A | 9/1992 | Weber et al. |
| 5,147,345 A | 9/1992 | Young et al. |
| 5,151,092 A | 9/1992 | Buell et al. |
| 5,156,793 A | 10/1992 | Buell et al. |
| D331,969 S | 12/1992 | Hunt |
| 5,167,653 A | 12/1992 | Igaue et al. |
| 5,167,655 A | 12/1992 | McCoy |

(56) References Cited

U.S. PATENT DOCUMENTS

| | | |
|---|---|---|
| 5,167,897 A | 12/1992 | Weber et al. |
| 5,171,236 A | 12/1992 | Dreier et al. |
| 5,178,139 A | 1/1993 | Angelillo et al. |
| D334,426 S | 3/1993 | Meis |
| 5,197,958 A | 3/1993 | Howell et al. |
| 5,214,442 A | 5/1993 | Roller |
| 5,221,274 A | 6/1993 | Buell et al. |
| 5,224,405 A | 7/1993 | Pohjola |
| 5,226,992 A | 7/1993 | Morman |
| 5,246,432 A | 9/1993 | Suzuki et al. |
| 5,246,433 A | 9/1993 | Hasse et al. |
| D341,197 S | 11/1993 | Patterson |
| 5,260,345 A | 11/1993 | Desmarais et al. |
| 5,266,592 A | 11/1993 | Grub et al. |
| 5,266,928 A | 11/1993 | Johnson |
| 5,269,775 A | 12/1993 | Freeland et al. |
| 5,275,103 A | 1/1994 | Hahne |
| 5,306,266 A | 4/1994 | Freeland |
| 5,318,555 A | 6/1994 | Siebers et al. |
| 5,320,891 A | 6/1994 | Levy et al. |
| 5,330,458 A | 7/1994 | Buell et al. |
| 5,330,459 A | 7/1994 | Lavon et al. |
| 5,336,545 A | 8/1994 | Morman |
| 5,342,338 A | 8/1994 | Roe |
| 5,342,343 A | 8/1994 | Kitaoka et al. |
| 5,344,516 A | 9/1994 | Tanji |
| 5,348,750 A | 9/1994 | Greenberg |
| 5,358,500 A | 10/1994 | Lavon et al. |
| 5,359,525 A | 10/1994 | Weyenberg |
| H1376 H | 11/1994 | Osborn |
| 5,380,313 A | 1/1995 | Goulait et al. |
| 5,387,207 A | 2/1995 | Dyer et al. |
| 5,397,316 A | 3/1995 | Lavon et al. |
| 5,397,318 A | 3/1995 | Dreier et al. |
| 5,407,439 A | 4/1995 | Goulait |
| 5,415,649 A | 5/1995 | Watanabe |
| 5,425,726 A | 6/1995 | Shimizu et al. |
| 5,428,076 A | 6/1995 | Roe |
| 5,435,010 A | 7/1995 | May |
| 5,456,176 A | 10/1995 | Strasser |
| 5,458,590 A | 10/1995 | Schleinz et al. |
| 5,460,622 A | 10/1995 | Dragoo et al. |
| 5,468,236 A | 11/1995 | Everhart |
| 5,470,639 A | 11/1995 | Gessner et al. |
| 5,500,063 A | 3/1996 | Jessup |
| 5,509,915 A | 4/1996 | Hanson et al. |
| 5,514,121 A | 5/1996 | Roe et al. |
| 5,518,801 A | 5/1996 | Chappell et al. |
| 5,540,671 A | 7/1996 | Dreier |
| 5,540,673 A | 7/1996 | Thomas et al. |
| 5,540,976 A | 7/1996 | Shawver et al. |
| 5,542,942 A | 8/1996 | Kline et al. |
| 5,554,142 A | 9/1996 | Dreier et al. |
| 5,554,143 A | 9/1996 | Roe et al. |
| 5,554,145 A | 9/1996 | Roe et al. |
| 5,567,609 A | 10/1996 | Sarras, Jr. et al. |
| 5,569,233 A | 10/1996 | Goulait |
| 5,569,234 A | 10/1996 | Buell et al. |
| 5,570,082 A | 10/1996 | Mahgerefteh et al. |
| 5,571,096 A | 11/1996 | Dobrin et al. |
| 5,580,411 A | 12/1996 | Nease et al. |
| 5,597,642 A | 1/1997 | Schleinz et al. |
| 5,607,760 A | 3/1997 | Roe |
| 5,608,119 A | 3/1997 | Amano et al. |
| 5,609,587 A | 3/1997 | Roe |
| 5,612,118 A | 3/1997 | Schleinz et al. |
| 5,622,581 A | 4/1997 | Ducker |
| 5,625,222 A | 4/1997 | Yoneda et al. |
| D379,226 S | 5/1997 | Kaczmarzyk et al. |
| 5,626,574 A | 5/1997 | Sasaki |
| 5,634,588 A | 6/1997 | Frode et al. |
| 5,635,191 A | 6/1997 | Roe et al. |
| 5,635,290 A | 6/1997 | Stopper et al. |
| 5,643,588 A | 7/1997 | Roe et al. |
| 5,649,914 A | 7/1997 | Glaug et al. |
| 5,653,703 A | 8/1997 | Roe et al. |
| 5,658,268 A | 8/1997 | Johns et al. |
| 5,659,538 A | 8/1997 | Stuebe et al. |
| 5,662,637 A | 9/1997 | Kitaoka et al. |
| 5,667,609 A | 9/1997 | Liu |
| 5,669,900 A | 9/1997 | Bullwinkel et al. |
| 5,681,298 A | 10/1997 | Brunner et al. |
| 5,685,874 A | 11/1997 | Buell et al. |
| 5,690,624 A | 11/1997 | Sasaki et al. |
| 5,702,376 A | 12/1997 | Glaug et al. |
| 5,735,839 A | 4/1998 | Kawaguchi |
| H1732 H | 6/1998 | Johnson |
| 5,766,212 A | 6/1998 | Jitoe |
| 5,766,389 A | 6/1998 | Brandon et al. |
| 5,769,838 A | 6/1998 | Buell et al. |
| 5,779,831 A | 7/1998 | Schmitz |
| 5,790,035 A | 8/1998 | Ho |
| 5,797,892 A | 8/1998 | Glaug et al. |
| 5,800,416 A | 9/1998 | Seger et al. |
| 5,818,719 A | 10/1998 | Brandon et al. |
| 5,843,057 A | 12/1998 | McCormack |
| 5,851,204 A | 12/1998 | Mizutani et al. |
| 5,865,823 A | 2/1999 | Curro |
| 5,883,028 A | 3/1999 | Morman et al. |
| 5,885,264 A | 3/1999 | Matsushita |
| 5,891,124 A | 4/1999 | Nomura et al. |
| 5,897,541 A | 4/1999 | Uitenbroek et al. |
| 5,897,545 A | 4/1999 | Kline et al. |
| 5,928,211 A | 7/1999 | Gustafsson |
| 5,931,827 A | 8/1999 | Buell et al. |
| 5,938,648 A | 8/1999 | Lavon et al. |
| 5,941,864 A | 8/1999 | Roe |
| 5,947,947 A | 9/1999 | Tanzer et al. |
| 5,957,908 A | 9/1999 | Kline et al. |
| 5,959,535 A | 9/1999 | Remsburg |
| 5,968,025 A | 10/1999 | Roe et al. |
| 5,977,430 A | 11/1999 | Roe et al. |
| 5,980,087 A | 11/1999 | Brandon et al. |
| 5,989,380 A | 11/1999 | Frischer |
| 5,997,520 A | 12/1999 | Ahr et al. |
| 5,997,989 A | 12/1999 | Gessner et al. |
| 6,001,460 A | 12/1999 | Morman et al. |
| 6,004,306 A | 12/1999 | Robles et al. |
| 6,010,490 A | 1/2000 | Freeland et al. |
| 6,013,063 A | 1/2000 | Roe et al. |
| 6,015,764 A | 1/2000 | Mccormack et al. |
| 6,017,537 A | 1/2000 | Alexander et al. |
| 6,033,502 A | 3/2000 | Coenen et al. |
| 6,045,543 A | 4/2000 | Pozniak et al. |
| 6,075,178 A | 6/2000 | La Wilhelm |
| 6,092,002 A | 7/2000 | Kastman et al. |
| 6,096,668 A | 8/2000 | Abuto et al. |
| 6,103,647 A | 8/2000 | Shultz et al. |
| 6,107,535 A | 8/2000 | Rossini et al. |
| 6,107,537 A | 8/2000 | Elder et al. |
| 6,114,597 A | 9/2000 | Romare |
| 6,118,041 A | 9/2000 | Roe et al. |
| 6,120,487 A | 9/2000 | Ashton |
| 6,120,488 A | 9/2000 | VanRijswijck et al. |
| 6,120,489 A | 9/2000 | Johnson et al. |
| 6,120,783 A | 9/2000 | Roe et al. |
| 6,123,694 A | 9/2000 | Pieniak et al. |
| 6,146,367 A | 11/2000 | Otsubo et al. |
| 6,153,209 A | 11/2000 | Vega et al. |
| 6,156,024 A | 12/2000 | Schulte et al. |
| 6,156,424 A | 12/2000 | Taylor |
| 6,166,285 A | 12/2000 | Schulte et al. |
| 6,168,584 B1 | 1/2001 | Allen et al. |
| 6,169,225 B1 | 1/2001 | Otsubo |
| 6,186,991 B1 | 2/2001 | Roe et al. |
| 6,214,788 B1 | 4/2001 | Velazco et al. |
| 6,224,699 B1 | 5/2001 | Bett et al. |
| 6,225,243 B1 | 5/2001 | Austin |
| 6,229,063 B1 | 5/2001 | Shimoe et al. |
| 6,253,159 B1 | 6/2001 | Bett et al. |
| 6,264,641 B1 | 7/2001 | Van Gompel et al. |
| 6,264,643 B1 | 7/2001 | Toyoda |
| 6,266,436 B1 | 7/2001 | Bett et al. |
| 6,267,974 B1 | 7/2001 | Suares et al. |

(56) References Cited

U.S. PATENT DOCUMENTS

| | | |
|---|---|---|
| 6,280,428 B1 | 8/2001 | Lash et al. |
| 6,297,424 B1 * | 10/2001 | Olson et al. ............... 604/361 |
| 6,297,434 B1 | 10/2001 | Martello |
| 6,307,119 B1 | 10/2001 | Cammarota |
| 6,313,372 B1 | 11/2001 | Suzuki |
| 6,320,096 B1 | 11/2001 | Inoue et al. |
| 6,328,982 B1 | 12/2001 | Shiroyama et al. |
| 6,348,253 B1 | 2/2002 | Daley et al. |
| 6,352,528 B1 | 3/2002 | Weber et al. |
| 6,359,168 B1 | 3/2002 | Frerot et al. |
| 6,384,728 B1 | 5/2002 | Kanor et al. |
| 6,428,526 B1 | 8/2002 | Heindel et al. |
| 6,429,526 B1 | 8/2002 | Blalock et al. |
| 6,432,098 B1 | 8/2002 | Kline et al. |
| 6,443,940 B1 | 9/2002 | Ashton et al. |
| 6,444,064 B1 | 9/2002 | Henry et al. |
| 6,448,467 B1 | 9/2002 | Herrlein et al. |
| 6,454,747 B1 | 9/2002 | Shimada et al. |
| 6,465,073 B1 | 10/2002 | Morman et al. |
| 6,478,786 B1 | 11/2002 | Glaug et al. |
| 6,479,154 B1 | 11/2002 | Walton et al. |
| 6,482,191 B1 | 11/2002 | Roe et al. |
| 6,503,236 B1 | 1/2003 | Uitenbroek et al. |
| 6,548,431 B1 | 4/2003 | Bansal et al. |
| 6,548,432 B1 | 4/2003 | Bansal et al. |
| 6,569,136 B1 | 5/2003 | Tao et al. |
| 6,576,810 B1 | 6/2003 | Underhill et al. |
| 6,579,274 B1 | 6/2003 | Morman et al. |
| 6,583,722 B2 | 6/2003 | Jeutter et al. |
| 6,590,136 B1 | 7/2003 | Young et al. |
| 6,592,884 B2 | 7/2003 | Hofmann et al. |
| 6,596,918 B1 | 7/2003 | Wehrle |
| 6,617,016 B2 | 9/2003 | Zhang et al. |
| 6,623,465 B1 | 9/2003 | Roe et al. |
| 6,623,837 B2 | 9/2003 | Morman et al. |
| 6,627,564 B1 | 9/2003 | Morman et al. |
| 6,627,786 B2 | 9/2003 | Roe et al. |
| 6,635,797 B2 | 10/2003 | Olson et al. |
| 6,642,427 B2 | 11/2003 | Roe et al. |
| 6,648,869 B1 | 11/2003 | Gillies et al. |
| 6,649,808 B1 | 11/2003 | Tao et al. |
| 6,657,100 B1 | 12/2003 | Underhill et al. |
| 6,676,646 B2 | 1/2004 | Bast et al. |
| 6,680,265 B1 | 1/2004 | Smith et al. |
| 6,680,422 B2 | 1/2004 | Roe |
| 6,692,475 B2 | 2/2004 | Mishima |
| 6,702,795 B2 | 3/2004 | Klemp |
| 6,710,221 B1 | 3/2004 | Pierce |
| 6,716,441 B1 | 4/2004 | Osborne et al. |
| 6,719,742 B1 | 4/2004 | Mccormack et al. |
| 6,726,668 B2 | 4/2004 | Underhill et al. |
| 6,727,404 B2 | 4/2004 | Ruman et al. |
| 6,733,483 B2 | 5/2004 | Raufman et al. |
| 6,743,314 B2 | 6/2004 | Henry et al. |
| 6,766,817 B2 | 7/2004 | Da Silva |
| 6,770,064 B1 | 8/2004 | Ruscher |
| 6,772,708 B2 | 8/2004 | Klofta |
| 6,811,865 B2 | 11/2004 | Morman et al. |
| 6,849,324 B2 | 2/2005 | Meece et al. |
| 6,870,479 B2 | 3/2005 | Gabriel |
| 6,875,710 B2 | 4/2005 | Eaton et al. |
| 6,881,206 B2 | 4/2005 | Underhill et al. |
| 6,884,906 B2 | 4/2005 | Dewis et al. |
| 6,902,793 B2 | 6/2005 | Ukegawa |
| 6,904,865 B2 | 6/2005 | Klofta et al. |
| 6,905,488 B2 | 6/2005 | Olson |
| 6,909,028 B1 | 6/2005 | Shawver et al. |
| 6,918,404 B2 | 7/2005 | Da Silva |
| 6,929,819 B2 | 8/2005 | Underhill et al. |
| 6,942,894 B2 | 9/2005 | Alberg et al. |
| 6,943,894 B2 | 9/2005 | Kitahara |
| 6,949,689 B2 | 9/2005 | Noda et al. |
| 6,955,733 B2 | 10/2005 | Miller et al. |
| 6,957,160 B2 | 10/2005 | Miller et al. |
| 6,958,432 B2 | 10/2005 | Underhill et al. |
| 6,960,834 B2 | 11/2005 | Nakamura et al. |
| 7,002,055 B2 | 2/2006 | Long et al. |
| 7,029,545 B2 | 4/2006 | Suzuki |
| 7,033,341 B2 | 4/2006 | Mishima |
| 7,056,411 B2 | 6/2006 | Desai et al. |
| 7,060,058 B2 | 6/2006 | Otsubo et al. |
| 7,066,586 B2 | 6/2006 | Da Silva |
| 7,108,759 B2 | 9/2006 | You |
| 7,112,193 B2 | 9/2006 | Otsubo |
| 7,118,558 B2 | 10/2006 | Wu |
| 7,123,981 B2 | 10/2006 | Dollevoet et al. |
| 7,169,137 B2 | 1/2007 | Shimada |
| 7,195,729 B2 | 3/2007 | Jackson et al. |
| 7,223,818 B2 | 5/2007 | Autran et al. |
| 7,255,688 B2 | 8/2007 | Sasaki |
| 7,285,255 B2 | 10/2007 | Kadlec et al. |
| 7,301,036 B2 | 11/2007 | Parmee et al. |
| 7,329,245 B2 | 2/2008 | Torigoshi |
| 7,361,802 B2 | 4/2008 | Ishikawa |
| 7,407,557 B2 | 8/2008 | Wada |
| 7,449,015 B2 | 11/2008 | Otsubo |
| 7,465,367 B2 | 12/2008 | Day |
| 7,520,873 B2 | 4/2009 | Sosalla et al. |
| 7,530,972 B2 | 5/2009 | Ando |
| 7,621,900 B2 | 11/2009 | Van Gompel |
| 7,754,627 B2 | 7/2010 | Mukai |
| 7,806,880 B2 | 10/2010 | Roe et al. |
| 7,895,718 B2 | 3/2011 | Horn |
| 8,003,846 B2 | 8/2011 | Strannemalm |
| 8,211,077 B2 | 7/2012 | Sugiyama et al. |
| 8,308,706 B2 | 11/2012 | Fukae |
| 8,388,596 B2 | 3/2013 | Horn |
| 8,475,424 B2 | 7/2013 | Fujimoto et al. |
| 9,913,761 B2 | 3/2018 | Trennepohl et al. |
| 2002/0062117 A1 | 5/2002 | Raufman et al. |
| 2002/0111596 A1 | 8/2002 | Fletcher et al. |
| 2002/0138062 A1 | 9/2002 | Kuen et al. |
| 2003/0028165 A1 | 2/2003 | Curro et al. |
| 2003/0060794 A1 | 3/2003 | Olson |
| 2003/0065298 A1 | 4/2003 | Krishnaswamy et al. |
| 2003/0073966 A1 | 4/2003 | Sosalla |
| 2003/0077430 A1 | 4/2003 | Grimm et al. |
| 2003/0087059 A1 | 5/2003 | Jackson et al. |
| 2003/0088220 A1 | 5/2003 | Molander et al. |
| 2003/0091807 A1 | 5/2003 | Desai et al. |
| 2003/0114807 A1 | 6/2003 | Underhill et al. |
| 2003/0114821 A1 | 6/2003 | Underhill et al. |
| 2003/0120240 A1 | 6/2003 | Buell et al. |
| 2003/0125682 A1 | 7/2003 | Olson et al. |
| 2003/0125689 A1 | 7/2003 | Olson et al. |
| 2003/0145937 A1 | 8/2003 | Underhill et al. |
| 2003/0158532 A1 | 8/2003 | Magee |
| 2003/0158534 A1 | 8/2003 | Niki et al. |
| 2003/0162458 A1 | 8/2003 | Tsujiyama et al. |
| 2003/0167049 A1 | 9/2003 | Gibbs |
| 2003/0193113 A1 | 10/2003 | Glovatsky |
| 2003/0199845 A1 | 10/2003 | Roe et al. |
| 2003/0233082 A1 | 12/2003 | Kline et al. |
| 2004/0030310 A1 | 2/2004 | Roe et al. |
| 2004/0064113 A1 | 4/2004 | Erdman |
| 2004/0067970 A1 | 4/2004 | Foster et al. |
| 2004/0071780 A1 | 4/2004 | Lillard et al. |
| 2004/0081680 A1 | 4/2004 | Pesce et al. |
| 2004/0082654 A1 | 4/2004 | Pesce et al. |
| 2004/0087059 A1 | 5/2004 | Ruby et al. |
| 2004/0088220 A1 | 5/2004 | Knight et al. |
| 2004/0091807 A1 | 5/2004 | Qian et al. |
| 2004/0092902 A1 | 5/2004 | Hoffman et al. |
| 2004/0102757 A1 | 5/2004 | Olson |
| 2004/0108054 A1 | 6/2004 | Otsubo et al. |
| 2004/0110442 A1 | 6/2004 | Rhim et al. |
| 2004/0127876 A1 | 7/2004 | Stevens |
| 2004/0132374 A1 | 7/2004 | Kobayashi |
| 2004/0143231 A1 | 7/2004 | Nair et al. |
| 2004/0162458 A1 | 8/2004 | Green et al. |
| 2004/0162536 A1 | 8/2004 | Becker et al. |
| 2004/0167486 A1 | 8/2004 | Busam et al. |
| 2004/0191118 A1 | 9/2004 | Mody |
| 2004/0191279 A1 | 9/2004 | Klofta |

(56) References Cited

U.S. PATENT DOCUMENTS

| | | |
|---|---|---|
| 2004/0193113 A1 | 9/2004 | Gillis et al. |
| 2004/0193133 A1 | 9/2004 | Desai et al. |
| 2004/0211696 A1 | 10/2004 | Underhill et al. |
| 2004/0220540 A1 | 11/2004 | Underhill et al. |
| 2004/0243083 A1* | 12/2004 | Matsuda et al. ......... 604/385.01 |
| 2004/0254549 A1 | 12/2004 | Olson et al. |
| 2004/0254550 A1 | 12/2004 | Huang et al. |
| 2005/0027274 A1 | 2/2005 | Suzuki et al. |
| 2005/0049553 A1 | 3/2005 | Triplett et al. |
| 2005/0049568 A1 | 3/2005 | Underhill et al. |
| 2005/0065489 A1 | 3/2005 | Driskell et al. |
| 2005/0096612 A1 | 5/2005 | Davis et al. |
| 2005/0096618 A1 | 5/2005 | Magee et al. |
| 2005/0106980 A1 | 5/2005 | Abed et al. |
| 2005/0124952 A1 | 6/2005 | Zehner et al. |
| 2005/0125877 A1 | 6/2005 | Benjamin et al. |
| 2005/0125923 A1 | 6/2005 | Benjamin et al. |
| 2005/0129743 A1 | 6/2005 | Benjamin et al. |
| 2005/0139713 A1 | 6/2005 | Weber et al. |
| 2005/0147785 A1 | 7/2005 | Ahn et al. |
| 2005/0177123 A1 | 8/2005 | Catalan |
| 2005/0203479 A1 | 9/2005 | Sakaguchi |
| 2005/0214461 A1 | 9/2005 | Desai et al. |
| 2005/0222546 A1 | 10/2005 | Vargo et al. |
| 2005/0228349 A1 | 10/2005 | Long et al. |
| 2005/0273071 A1 | 12/2005 | McKiernan et al. |
| 2006/0004333 A1 | 1/2006 | Olson |
| 2006/0025737 A1 | 2/2006 | Song et al. |
| 2006/0030831 A1* | 2/2006 | Matsuda ........... A61F 13/15699 604/392 |
| 2006/0047260 A1 | 3/2006 | Ashton et al. |
| 2006/0068168 A1 | 3/2006 | Olson et al. |
| 2006/0069361 A1 | 3/2006 | Olson et al. |
| 2006/0069362 A1 | 3/2006 | Odorzynski et al. |
| 2006/0111686 A1 | 5/2006 | Schneider |
| 2006/0142728 A1 | 6/2006 | Tabor |
| 2006/0173436 A1* | 8/2006 | Krautkramer et al. ....... 604/393 |
| 2006/0212010 A1 | 9/2006 | Roe et al. |
| 2006/0212018 A1 | 9/2006 | Roe et al. |
| 2006/0224132 A1 | 10/2006 | Roe et al. |
| 2006/0247594 A1 | 11/2006 | Nickel et al. |
| 2006/0264858 A1 | 11/2006 | Roe et al. |
| 2006/0293632 A1 | 12/2006 | Long et al. |
| 2007/0005035 A1 | 1/2007 | Snauwaert et al. |
| 2007/0032766 A1* | 2/2007 | Liu et al. .................... 604/361 |
| 2007/0049884 A1* | 3/2007 | Long et al. .................. 604/361 |
| 2007/0073261 A1 | 3/2007 | Ashton et al. |
| 2007/0083173 A1 | 4/2007 | Olson |
| 2007/0112322 A1 | 5/2007 | Ashton et al. |
| 2007/0142800 A1 | 6/2007 | Liu |
| 2007/0191797 A1 | 8/2007 | Roe et al. |
| 2007/0233025 A1 | 10/2007 | Nishikawa et al. |
| 2007/0233026 A1 | 10/2007 | Roe et al. |
| 2007/0233027 A1 | 10/2007 | Roe et al. |
| 2007/0233028 A1 | 10/2007 | Roe et al. |
| 2007/0250406 A1 | 10/2007 | Mason et al. |
| 2007/0287348 A1 | 12/2007 | Autran et al. |
| 2007/0287971 A1 | 12/2007 | Roe et al. |
| 2007/0287982 A1 | 12/2007 | Lodge et al. |
| 2007/0287983 A1 | 12/2007 | Lodge et al. |
| 2008/0004585 A1 | 1/2008 | McCusker, III et al. |
| 2008/0009817 A1* | 1/2008 | Norrby ...................... 604/385.3 |
| 2008/0167635 A1 | 1/2008 | Kline |
| 2008/0087569 A1 | 4/2008 | Ponomarenko et al. |
| 2008/0091162 A1 | 4/2008 | Maldonado et al. |
| 2008/0108967 A1 | 5/2008 | Mizushima et al. |
| 2008/0132872 A1* | 6/2008 | Trennepohl ....... A61F 13/15699 604/385.24 |
| 2008/0134487 A1 | 6/2008 | Hartono |
| 2009/0030389 A1 | 1/2009 | Ashton et al. |
| 2009/0036860 A1 | 2/2009 | Sugiyama et al. |
| 2009/0254058 A1 | 10/2009 | Shiriike et al. |
| 2010/0076394 A1 | 3/2010 | Hayase |
| 2010/0089264 A1 | 4/2010 | Warner |
| 2010/0106123 A1 | 4/2010 | Fukae |
| 2010/0298799 A1 | 11/2010 | Wheeler |
| 2011/0077609 A1 | 3/2011 | Kuwano et al. |
| 2013/0096528 A1 | 4/2013 | Hashino et al. |

FOREIGN PATENT DOCUMENTS

| | | |
|---|---|---|
| EP | 0 418 052 | 3/1991 |
| EP | 0 495 285 | 7/1992 |
| EP | 0 454 105 B1 | 11/1995 |
| EP | 0 547 497 B1 | 3/1997 |
| EP | 1102571 B1 | 8/1998 |
| EP | 0873738 | 10/1998 |
| EP | 0 951 889 | 10/1999 |
| EP | 1179330 | 8/2000 |
| EP | 1184012 | 9/2000 |
| EP | 1269955 B1 | 6/2001 |
| EP | 0 776 645 B1 | 3/2002 |
| EP | 1184012 | 3/2002 |
| EP | 1 216 673 A1 | 6/2002 |
| EP | 1 222 907 A2 | 7/2002 |
| EP | 1 287 799 A2 | 3/2003 |
| EP | 1 356 798 A1 | 10/2003 |
| EP | 0 937 446 B1 | 9/2004 |
| EP | 1 279 357 B1 | 9/2005 |
| GB | 2 177 977 | 2/1987 |
| JP | 56-043402 | 4/1981 |
| JP | 02-140163 | 5/1990 |
| JP | H4144558 | 5/1992 |
| JP | 05-247701 | 9/1993 |
| JP | H10298801 | 11/1998 |
| JP | 11-104172 | 4/1999 |
| JP | 2000000266 | 1/2000 |
| JP | 2003070838 | 8/2001 |
| JP | 2003-111798 | 4/2003 |
| JP | 2004-141640 A | 5/2004 |
| JP | 2004-305761 | 11/2004 |
| JP | 2008-136515 | 11/2006 |
| JP | 2007-000654 | 1/2007 |
| JP | 2007-029609 | 2/2007 |
| JP | 2008-523883 | 7/2008 |
| JP | 3045174 | 7/2008 |
| JP | 2006-130140 | 7/2009 |
| JP | 2009-160129 | 7/2009 |
| JP | 2011254996 | 12/2011 |
| WO | WO 1994/013235 A1 | 6/1994 |
| WO | WO 1994/014395 A1 | 7/1994 |
| WO | WO 1995/016746 A1 | 6/1995 |
| WO | WO 1996/010380 A2 | 4/1996 |
| WO | WO-1996/031178 | 10/1996 |
| WO | WO 1999/020216 A1 | 4/1999 |
| WO | WO 1999/022688 A1 | 5/1999 |
| WO | WO2000037003 A2 | 11/1999 |
| WO | WO 2000/000233 A1 | 1/2000 |
| WO | WO 2000/015169 A1 | 3/2000 |
| WO | WO 2000/035401 A1 | 6/2000 |
| WO | WO 2000/037006 A1 | 6/2000 |
| WO | WO 2000/037009 | 6/2000 |
| WO | WO 2000/076438 | 12/2000 |
| WO | WO 2000/076439 | 12/2000 |
| WO | WO 2000/076442 | 12/2000 |
| WO | WO 2000/076443 | 12/2000 |
| WO | WO101904 | 1/2001 |
| WO | WO 2001/021126 A1 | 3/2001 |
| WO | WO 2001/041691 A1 | 6/2001 |
| WO | WO 2001/095845 A1 | 12/2001 |
| WO | WO 2002/049564 A1 | 6/2002 |
| WO | WO 2002/091968 A2 | 11/2002 |
| WO | WO 2003/034966 A1 | 5/2003 |
| WO | WO 2004/026206 A1 | 4/2004 |
| WO | WO 2004/028403 A2 | 4/2004 |
| WO | WO 2004/071780 A2 | 8/2004 |
| WO | WO-2004/105664 | 12/2004 |
| WO | WO-2004/105665 | 12/2004 |
| WO | WO 2005/037159 A | 4/2005 |
| WO | WO 2005/041834 A1 | 5/2005 |
| WO | WO 2005/102239 A1 | 11/2005 |
| WO | WO 2006/017518 A2 | 2/2006 |
| WO | WO 2006/017674 A1 | 2/2006 |
| WO | WO 2006/028911 A1 | 3/2006 |

(56) References Cited

FOREIGN PATENT DOCUMENTS

| WO | WO 2006/127519 A2 | 11/2006 |
| WO | WO 2007/017817 A2 | 2/2007 |
| WO | WO2009067055 A1 | 11/2007 |
| WO | WO-2009/084643 | 9/2009 |

OTHER PUBLICATIONS

Timothy R. Schum, MD, et al.—Sequential Acquisition of Toilet-Training Skills: A Descriptive Study of Gender and Age Differences in Normal Children, Pediatrics, Mar. 2002, 7 pages vol. 109, No. 3.
Photos of Pampers Trainers pants and packages.
International Search Report, PCT/CN2013/074721, dated Aug. 1, 2013.
Supplemental International Search Report, PCT/CN2013/074721, dated Mar. 21, 2014.

* cited by examiner

ABSORBENT ARTICLE HAVING CHARACTERISTIC WAIST ENDS

CROSS REFERENCE TO RELATED APPLICATION

This application claims priority to Chinese Patent Application Number 2012/075490, filed on May 15, 2012, and Chinese Patent Application Number 2013/074721, filed on Apr. 25, 2013, the substances of which are incorporated herein by reference.

FIELD

The present invention relates to absorbent articles having characteristic waist ends.

BACKGROUND

Infants and other incontinent individuals wear disposable absorbent articles such as diapers to receive and contain urine and other body exudates. Training pants or pull-on diapers have become popular for use on children able to walk and often who are toilet training. Many disposable pull-on garments use elastic elements secured in an elastically contractible condition in the waist and/or leg openings. Typically, in order to insure full elastic fit about the leg and the waist such as is provided with durable undergarments, the leg openings and waist opening are encircled at least in part with elasticized bands positioned along the periphery of the respective opening.

Disposable absorbent articles having an absorbent main body to cover the crotch region of the wearer and a separate elastic belt defining the waist opening and leg opening are known in the art. Such articles, compared to articles where the outer cover completely covers the entirety of the garment-facing surface of the article, may be advantageous in that they may have better breathability by having less layers of material in certain areas of the articles, and that they may be manufactured economically. On the other hand, in that the number of layers of material used for making the absorbent article may decrease towards the waist opening, the waist ends typically have a translucent appearance of less thickness. Such translucent look and thin feel around the waist ends may deviate from that of a durable undergarment which would usually be thicker at the waist ends than the remainder of the garment. Further, the translucent look and thin feel may be associated with a cheap image or low quality of the article.

Based on the foregoing, there is a need for a disposable absorbent article to provide an undergarment-like look and feel. There is also a need for providing such an absorbent article without compromise to the performance as an absorbent article, such as fit, wearability, comfort during wear, prevention of sagging, and prevention of leakage. There is further a need for providing such an absorbent article in an economical manner.

SUMMARY

The present disclosure is directed to an absorbent article continuous in a longitudinal direction and a transverse direction, comprising a front belt portion, a back belt portion, and an absorbent main body, the center of the front belt portion is joined to a front waist panel of the absorbent main body, the center of the back belt portion is joined to a back waist panel of the absorbent main body, the front and back belt portion each having a left side panel and a right side panel where the absorbent main body does not overlap, and the respective left and right side panels of the front belt portion and the back belt portion are joined with each other only at the respective transverse edges to form a waist opening and two leg openings, each front belt portion and back belt portion having transversely continuous proximal and distal edges, the proximal edge being located closer than the distal edge relative to the longitudinal center of the article, wherein:

the absorbent main body comprises a main body graphic zone;

the front belt portion and the back belt portion each have a waist end region adjacent the waist opening, wherein the front and back waist panels of the absorbent main body do not overlap with the front or back waist end regions;

the front belt portion and the back belt portion each have a leg end region adjacent the proximal edges;

the left and right side panels of the front belt portion and the back belt portion each have a tummy belt region between the waist end region and the leg end region;

the waist end region having an opacity of at least 15 points greater than that of the tummy belt region.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings and which like designations are used to designate substantially identical elements, and in which:

FIGS. 4 (a), (b), and (c) are embodiments of a schematic cross-sectional view of FIG. 2 taken along the line IV-IV of the present invention.

FIG. 4 (d) is an schematic cross-sectional view of FIG. 2 taken along the line IV-IV of the prior art.

DETAILED DESCRIPTION

Various non-limiting embodiments of the present invention will now be described to provide an overall understanding of the principles of the structure, function, manufacture, and use of the apparatuses, methods, and articles disclosed herein. One or more examples of these non-limiting embodiments are illustrated in the accompanying drawings. Those of ordinary skill in the art will understand that the apparatuses and methods specifically described herein and illustrated in the accompanying drawings are non-limiting example embodiments and that the scope of the various non-limiting embodiments of the present invention are defined solely by the claims. The features illustrated or described in connection with one non-limiting embodiment may be combined with the features of other non-limiting embodiments. Such modifications and variations are intended to be included within the scope of the present invention.

As used herein, the term "absorbent article" refers to articles of wear to absorb and contain various exudates such as urine, feces, and menses discharged from the body, and may be in the form of pants, taped diapers, incontinent briefs, feminine hygiene garments, and the like. The absorbent article made partly by the elastic member cutting roll system or the continuous process described above may have a defined waist opening and a pair of leg openings and which are pulled onto the body of the wearer by inserting the legs into the leg openings and pulling the article up over the waist. An example absorbent article 20 is shown in FIG. 1.

Figure 1:
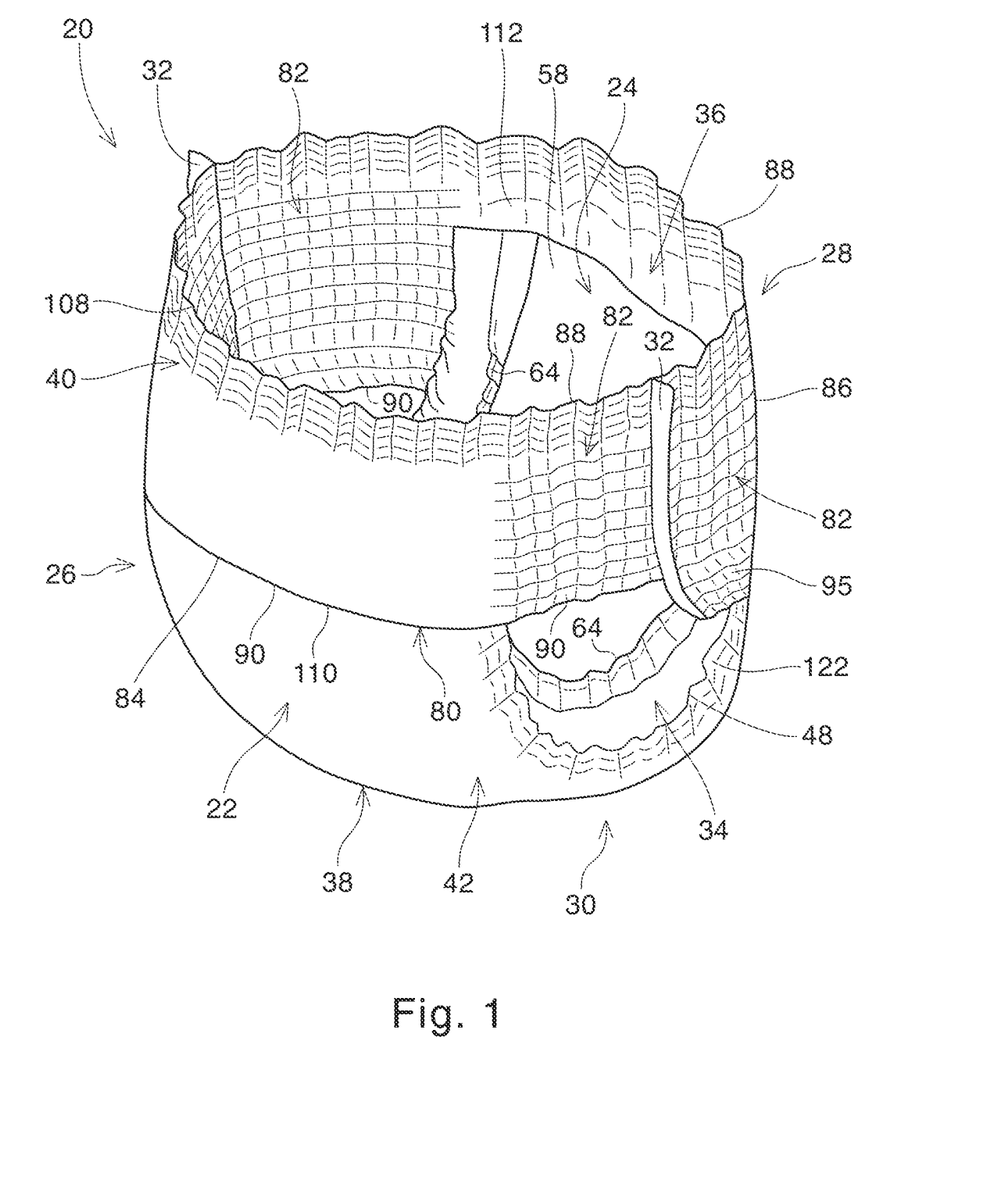
FIG. 1 is a perspective view of one embodiment of an absorbent article of the present invention.
Figure 2:
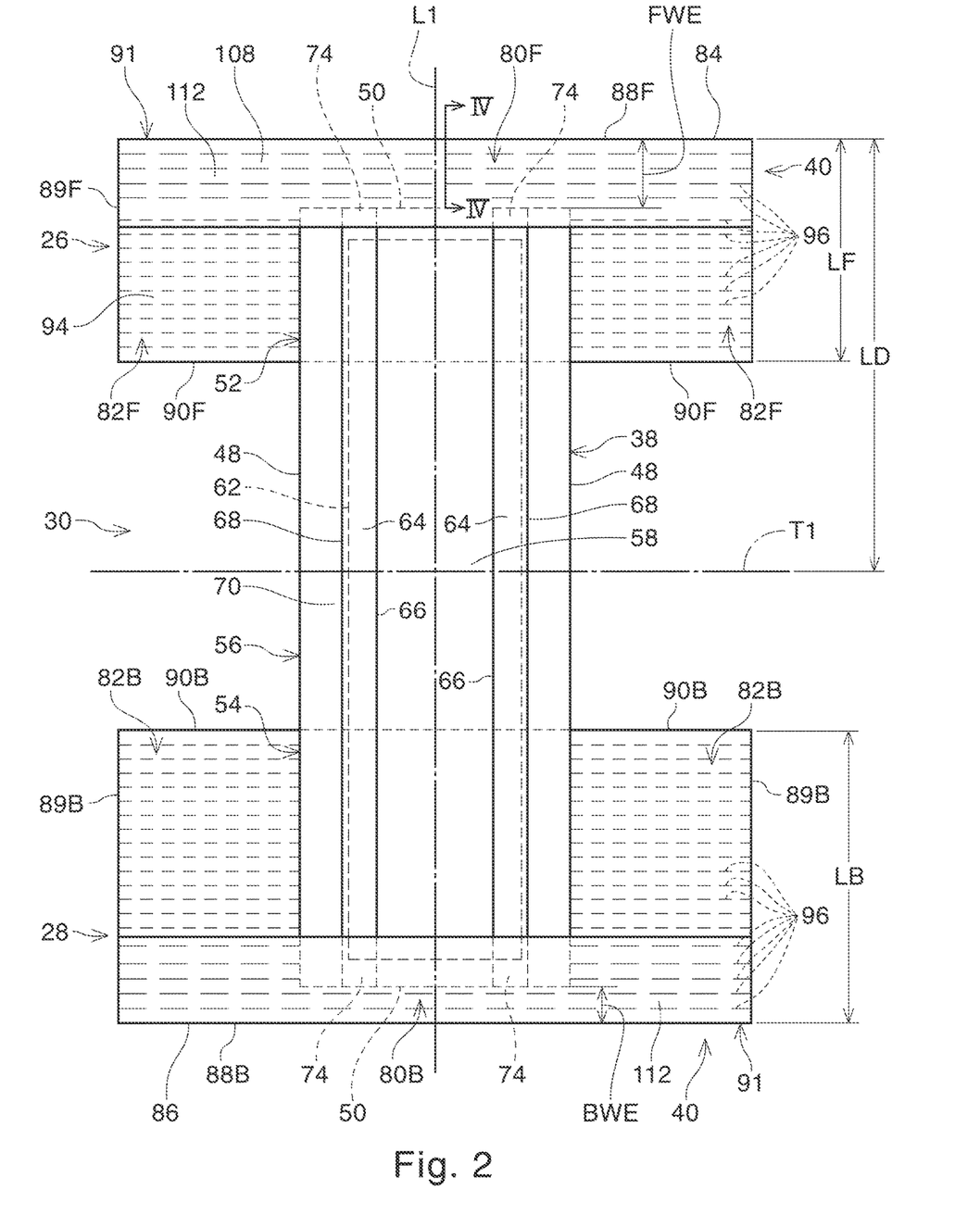
FIG. 2 is a top plan view of one embodiment of an absorbent article of the present invention in a flat uncontracted condition showing the inner, body facing surface.

FIG. 1 is a perspective view of an embodiment of the absorbent article 20 of the present invention and FIG. 2 is a top plan view of the same article in its flat uncontracted condition showing the inner, body-facing surface. The absorbent article 20 has a longitudinal centerline L1 and a transverse centerline T1. The absorbent article 20 has an outer surface 22, an inner surface 24 opposed to the outer surface 22, a front region 26, a back region 28, a crotch region 30, and seams 32 which join the front region 26 and the back region 28 to form two leg openings 34 and a waist opening 36. The absorbent article 20 comprises an absorbent main body 38 (hereinafter may be referred to as "main body") to cover the crotch region of the wearer, a front belt portion 84 and a back belt portion 86 (hereinafter may be referred to as "front and back belt portion 84, 86), the front and back belt portions forming a ring-like belt 40 (hereinafter may be referred to as "belt") extending transversely defining the waist opening 36. The front and back belt portions and the main body 38 jointly define the leg openings 34.

Figure 3:
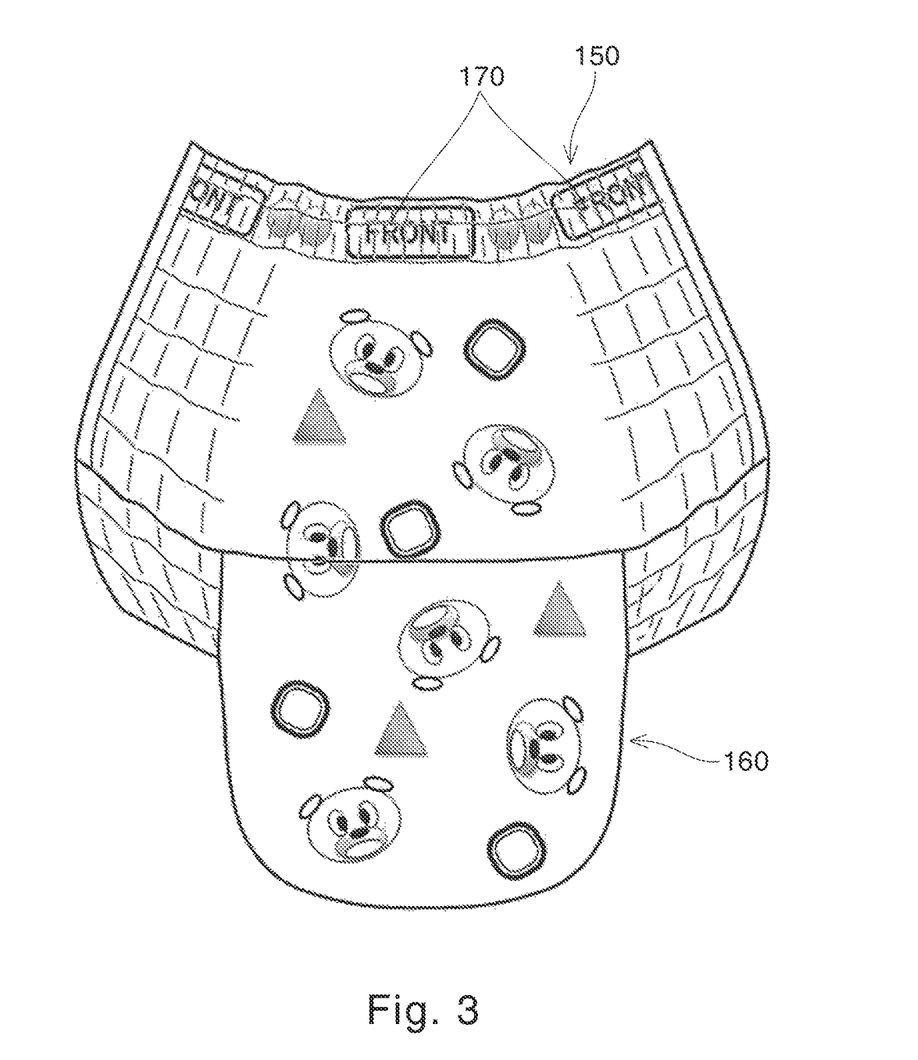
FIG. 3 is a schematic view of one embodiment of an absorbent article of the present invention observed from the front of the article.

The absorbent main body 38 absorbs and contains body exudates disposed on the main body 38. In the embodiment shown in FIG. 2, the main body 38 has a generally rectangular shape, left and right longitudinally extending side edges 48 (hereinafter may be referred to as "longitudinal side edge") and front and back transversely extending end edges 50 (hereinafter may be referred to as "transverse end edge"). The main body 38 also has a front waist panel 52 positioned in the front region 26 of the absorbent article 20, a back waist panel 54 positioned in the back region 28, and a crotch panel 56 between the front and back waist panels 52, 54 in the crotch region 30. The center of the front belt portion 84 is joined to a front waist panel 52 of the absorbent main body, the center of the back belt portion 86 is joined to a back waist panel 54 of the absorbent main body, the front and back belt portion 84, 86 each having a left side panel and a right side panel where the absorbent main body does not overlap. Referring to FIG. 3, the main body 38 may comprise a main body graphic zone 160. Among the materials for making the main body 38, the material on which the main body graphic zone is disposed, and which is visible from the garment facing surface, is called a graphic sheet. The graphic sheet may be the outermost layer of the absorbent main body, or a layer inside of a transparent or translucent outer layer through which the graphics may be observed. The main body graphic zone 160 may comprise a tummy graphic zone disposed in the front or back waist panel, and a leg graphic zone (not shown) disposed adjacent a leg opening extending circumferentially about at least a portion of the leg opening. At least two selected from the group consisting of the waist graphic zone (hereinafter described), the tummy graphic zone, and the leg graphic zone, may be coordinated with one another to create a uniform graphical element, such as common colors, patterns, articles, characters, associated shapes, etc.

Referring to FIGS. 1 and 2, the ring-like belt 40 formed by the front belt portion 84 and back belt portion 86 acts to dynamically create fitment forces and to distribute the forces dynamically generated during wear. Herein, the term "proximal" is used to indicate the position of a "proximal" portion being closer relative to the longitudinal center of the article, also closer relative to the crotch panel of the main body than the position of a "distal" portion. Therefore, the proximal edge 90F, 90B is located closer than the distal edge 88F, 88B relative to the crotch panel 56 of the main body 38. The front and back belt portions 84, 86 may be joined with each other only at the front and back side edges 89F, 89B at the seams 32 to form a absorbent article having a waist opening 36 and two leg openings 34. In one embodiment, the front and back belt portions are not continuous with one another in the crotch region. In such embodiment, there is no material that covers the entirety of either the wearer-facing surface or garment-facing surface of the article. The front central panel 80F may partly overlap with the front waist panel 52 of the main body 38. The back central panel 80B may partly overlap with the back waist panel 54 of the main body 38. However, the central panel 80F, 80B may not extend into the crotch panel 56 of the main body 38 and not disposed in the crotch panel 56. In the embodiment shown in FIG. 2, the central panel 80F, 80B partly overlaps with and is joined to the front waist panel 52 and the back waist panel 54, respectively.

The front belt portion 84 comprises a front waist end region ("FWE" as shown in FIG. 2) adjacent the waist opening. The front waist end region may exist where the front waist panel 52 of the main body 38 does not overlap with the front belt portion 84. The back belt portion 86 comprises a back waist end region ("BWE" as shown in FIG. 2) adjacent the waist opening. The back waist end region may exist where the back waist panel 54 of the main body does not overlap with the back belt portion 86. The longitudinal length of the waist end region may be 5-100 mm, or 5-50 mm, or 10-30 mm. The longitudinal length of the front waist end region and the back waist end region may be the same or different. The front belt portion 84 and back belt portion 86 may each comprise a leg end region adjacent the proximal edges (not shown). The longitudinal length of the leg end region may be 5-30 mm, or 5-20 mm, or 10-15 mm. The longitudinal length of the front leg end region and the back leg end region may be the same or different. The left and right side panels of the front belt portion 84 and the back belt portion 86 may each comprise a left and right tummy belt region between the waist end region and the leg end region. The tummy belt region may be made with minimum material for providing an elastic panel, such as two layers of low caliper non-woven material and elastic strands sandwiched between them. Such configuration may provide good fitment and breathability of the article. Referring to FIG. 3, at least the front waist end region or the back waist end region may comprise a waist graphic zone 150, and the waist graphic zone may comprise an indicia 170. The waist graphic zone may extend circumferentially about the front and back waist end regions. Indicia 170 include one or more of indication of front and/or back of the article, size, gender, pulling area, brand name, logo, and others. In one embodiment, the indica 170 is an indication of front and/or back of the article. The front leg end region or the back leg end region may comprise a leg end graphic zone. The leg end graphic zone may be coordinated with the leg graphic zone on the main body to create a continuous look for the leg opening.

Figure 4:
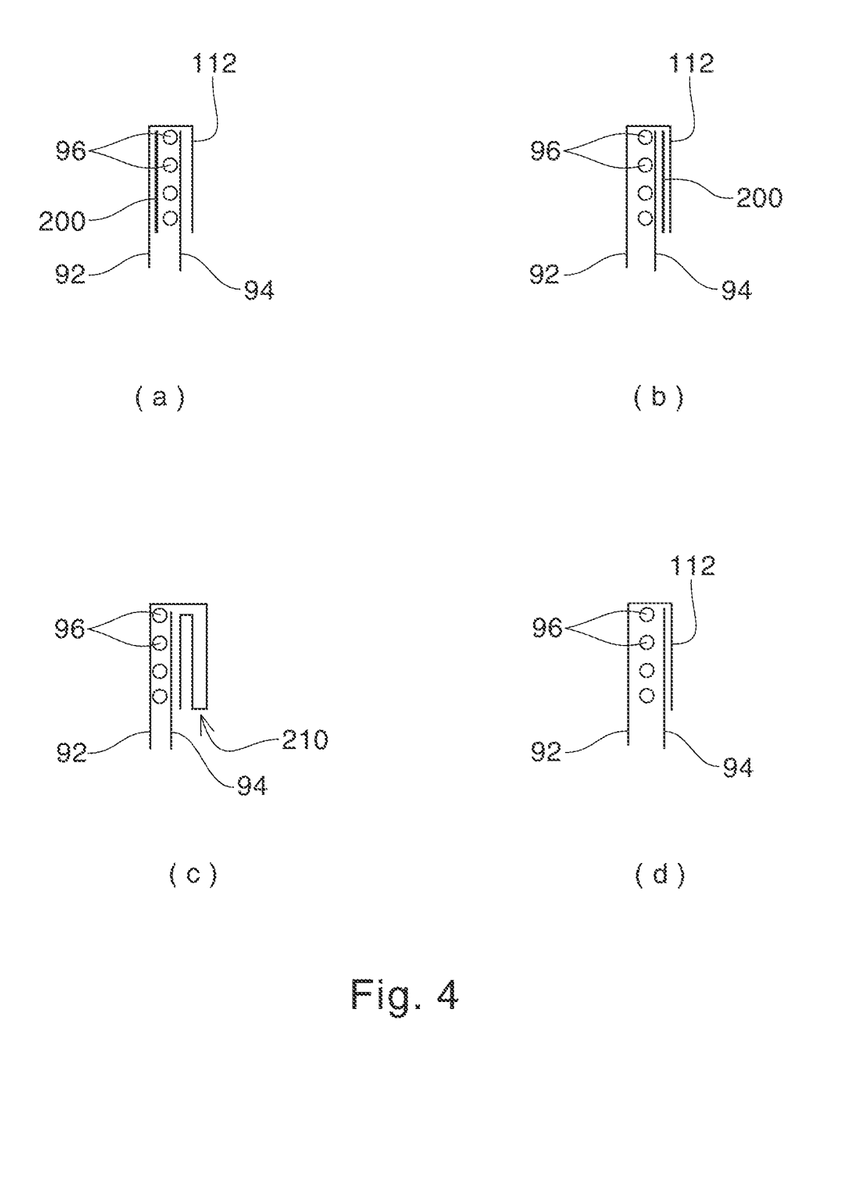

Referring to FIGS. 2, 4 (a), (b), and (c), the front belt portion 84 and back belt portion 86 may each comprise an inner sheet 94, an outer sheet 92, (hereinafter also collectively "belt sheets") and a plurality of elastic strands 96 sandwiched between the inner and outer sheets, the elastic strands 96 extending in the transverse direction to provide a continuous elastic ring when the front belt portion and the back belt portion are joined. The waist end region may overlap with one or more elastic strands. The waist end region may overlap with 1-5 elastic strands, or 2-5 elastic strands. The leg end region may overlap with one or more elastic strands. The leg end region may overlap with 1-3 elastic strands, or 2-3 elastic strands. In one embodiment, the outer sheet 92 of the front or back belt portion towards the distal edge 108 may be longer than the size of the inner sheet 94 in the longitudinal direction, and an end flap 112 of the outer sheet 92 may be folded over the distal end of the inner sheet 94 at the waist opening 36 to form the waist end region. Similarly, an end flap 112 of the outer sheet 92 towards the proximal edge may be folded over the proximal end of the inner sheet 94 to form the leg end region. Both outer sheets 92 of the front belt portion 84 and the back belt portion 86 may be folded to cover both the front proximal edge 90F and the back proximal edge 90B. The waist graphic zone may be disposed on material in the waist end regions, so long as it is visible from the garment side of the article. The leg end graphic zone may be disposed on material in the leg end regions, so long as at least a portion is visible from the garment side of the article. The material on which the waist graphic zone and leg end graphic zone are disposed may be the same or different material for also adding opacity and/or thickness to the waist end regions and leg end regions. In one embodiment, they are the same material. The front and back belt portions 84, 86 may be provided in low caliper non-woven material for sake of breathability and softness of the belt 40. Such low caliper non-woven material, however, may provide a thin feel and transparent look at the waist end region, which may not provide an under-garment like feel and look. Opacity of nonwoven material may be measured according to the EDANA ERT110 1 (78) test method. Opacity is described in the unit of percentage. Such numerical value is described as points herein. For purposes of measuring opacity, the sample materials are prepared in an un-gathered state, with any elastic strands removed, if elastic strands are used or planned to be used. The waist end region and leg end region may have an opacity of at least 15 points greater than, or at least 20 points greater than, or at least 30 points greater than, or at least 40 points greater than, or 10-50 points greater than that of the tummy belt region. By adding material to the waist end region and/or leg end region, an under-garment like feel and look may be achieved while maintaining the overall performance of the belt 40. Further, by selection of the material, skin gather marking at the waist opening or leg opening may be alleviated, and fit of the waist opening or leg opening may be improved. Any material which meets the opacity requirement or provides the desired skin/fit benefit may be added to the waist end region or the leg end region.

As in FIGS. 4(a) and 4(b), in some embodiments, the waist end region and leg end region may comprise an additional material 200 disposed between the inner sheet and the outer sheet. As in FIG. 4(c), in some embodiments, the waist end region and leg end region may comprise an extension of the end flap of the outer sheet folded over the waist opening and further disposed in at least three layers. The configurations of FIGS. 4 (a), (b), and (c) are advantageous in that such additional material or multiple layers of the outer sheet in the waist end regions and leg end regions may provide added thickness and opacity (non-translucency) to the waist end region and leg end region. The additional material 200 provided in the waist end region and leg end region may comprise a cushion material such as polyurethane and corrugated non-woven, or elastic material such as elastomeric film, to provide additional sensorial elements to the waist end region and leg end region. Sensorial elements include tackiness, resilience, softness, lubricity, and others. Further, adding thickness to the waist end region may help prevent flipping of the waist end region over the waist edge. Adding material of certain tackiness or resilience may improve the fit of the leg opening. Adding material of certain softness or lubricity may prevent or alleviate gathering marks at the waist end region or the leg end region.

Similar or different configurations for adding material for opacity and/or thickness may be taken for the waist end region and leg end regions. By having both the waist end region and leg end region have higher opacity and/or thickness than the tummy belt region, an under-garment like feel and look may be achieved.

In one embodiment, the back belt portion 86 has a greater longitudinal length LB between the back distal edge 88B and the back proximal edge 90B along its entire width of the back belt portion 86 in the transverse direction than the longitudinal length LF of the front belt portion 84 between the front distal edge 88F and the front proximal edge 90F (FIGS. 1 and 2). In such embodiment, when the absorbent article is assembled to form the waist opening 36 and the leg openings 34, the absorbent article 20 is folded along the transverse centerline T1 such that the front distal edge 88F is aligned with the back distal edge 88B. The front side edge 89F is also aligned with a portion of the back side edge 89B. Then the front belt portion 84 and the back belt portion 86 are joined at the front and back side edges 89F, 89B at the seams 32. The front and back proximal edges 90F, 90B, however, may not be aligned to one another. The back proximal edge 90B may be disposed longitudinally closer than the front proximal edge 90F relative to the transverse center line T1 such that the proximal portion of the back side panel 82B extends toward the crotch panel 56 of the main body 38 beyond the front proximal edge 90F. The side edge of the proximal portion of the back side panel 82B may not be joined to anywhere and free from attachment. Thus, the proximal portion of the back side panel 82B provides a buttock cover 95. Both outer sheets 92 of the front belt portion 84 and the back belt portion may be folded to cover both the front proximal edge 90F and the back proximal edge 90B. By such configuration for both the front and back portions of the leg opening, a relatively integral appearance of the leg opening may be achieved.

As described hereinabove, pant-type absorbent articles may have different configurations for the front and back of the article, including but not limited to, greater area of material in the back side for covering the buttock, uneven distribution of absorbent material in the main body for effectively absorbing and containing bodily fluids, etc. Unlike taped absorbent articles which may define the front and back of the article by the configuration of the tape and tape landing zone, the front and back distinction of a pant-type absorbent article may not be obvious to the wearer or care-giver just by the structure of the article. As such, the front and/or back side of the article may be clearly communicated to provide the expected performance of the article.

The present absorbent article may be suitably manufactured by forming the main body, and the front and back belt portions, and assembling the 3 elements. In processes where the main body and belt portions are formed in continuous direction that are perpendicular to each other, the main body provided in individual pieces is turned ninety degrees and placed on the continuous front and back belt portions at a predetermined interval to provide the left and right side panels between each of the individual main bodies. The process may then be followed by cutting the continuous front and back belt portions into each individual absorbent article, folding along the transverse centerline T1 in the crotch region, and joining the front and back belt portions 84, 86 at the seam 32 adjacent the side edges 89F, 89B to form the waist opening and the leg openings.

As need be, the main body graphic zone is registered with respect to the length of the individual main body or in relation to the front and back belt portions. By "registration" herein, what is meant is the act of aligning the position of one part of an article with another. Positioning may be in any direction. The graphic sheet on which the main body graphic zone is disposed may be registered with respect to the length of the individual main body or in relation to the front and back belt portions so that, for example, the tummy graphic zone matches with the designated front or back waist panel area, or so that the designated position for front and back indication is properly provided for the respective front and/or back belt portion to be joined to. When such registration is required, failure of registration may provide the tummy graphic zone in an undesired portion of the article, or provide wrong indication of the front and back side of the article.

In one embodiment, by providing a front/back indicia on either the front or back waist graphic zones, need for the above mentioned registration may become less critical. Absence of the registration need may simplify process steps, or reduce cost for machinery to conduct such registration. Further, absence of the need to register the main body graphic zone relative to the length of the main body, or the direction of the main body, allows the main body graphic zone to have a variety of graphics. The main body graphic zone may be one in a form of non-direction, such as repeating patterns, or characters disposed in plurality in random orientation. FIG. 3 shows one embodiment of a non-directional graphic for the main body graphic zone 160. Accordingly in one embodiment, the present invention is directed to a process of manufacturing the article herein wherein the process is free of a step of registering the main body graphic zone relative to the direction or positioning of the main body.

The obtained absorbent article of the present invention may provide an aesthetically pleasing, undergarment-like look and feel at the waist end edge. The obtained absorbent article of the present invention may also have a suitable tackiness, resilience, or softness at the waist end edge to enhance wearability by aiding pull up, or to provide good fit, or to prevent flipping of the waist end region over the waist edge, or to provide comfort during wear, or to prevent or alleviate gathering marks, or to prevent sagging and leakage. The obtained absorbent article of the present invention may be made in an economical manner.

Example 1

An absorbent article of the present invention having a waist end region according to FIG. 4 (a) was made. The opacity of the waist end region was 80.6%, and the opacity of the tummy belt region was 37.9% when measured according to the EDANA ERT110 1 (78) test method. Thus, the opacity of the waist end region was 42.7 points greater than that of the tummy belt region.

Comparative Example

An absorbent article of the prior art having the same configuration as that of Example 1, except having a waist end region according to FIG. 4 (d), was made. The opacity of the waist end region was 49.1%, and the opacity of the tummy belt region was 37.9% when measured according to the EDANA ERT110 1 (78) test method. Thus, the opacity of the waist end region was 11.2 points greater than that of the tummy belt region.

Compared to Comparative Example, Example 1 provided more of an undergarment-like look and feel at the waist end edge, without significant compromise to other performance as an absorbent article.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article continuous in a longitudinal direction and a transverse direction, comprising a front belt portion, a back belt portion, and an absorbent main body, the center of the front belt portion is joined to a front waist panel of the absorbent main body, the center of the back belt portion is joined to a back waist panel of the absorbent main body, the front belt portion comprising a pair of front side panels, and the back belt portion comprising a pair of back side panels, and the respective front side panels of the front belt portion and the back side panels of the back belt portion are joined with each other, interior surface to interior surface, only at the respective transverse side edges to form side seams and a waist opening and two leg openings, each front belt portion and back belt portion having transversely continuous proximal and distal end edges, the proximal end edges being located closer than the distal end edges relative to the longitudinal center of the article, wherein:

the front belt portion having a front waist end region (FWE) defined between a transversely extending front end edge of the absorbent main body and a front distal edge of the absorbent article;

the back belt portion having a back waist end region (BWE) defined between a transversely extending back end edge of the absorbent main body and a back distal edge of the absorbent article;

wherein the front and back distal end edges of the front and back belt portions are parallel to each other and wherein the front and back proximal end edges of the front and back belt portions are parallel to each other;

wherein the FWE and the BWE are not equal distances;

wherein the front belt portion comprises a front inner sheet and a front outer sheet, wherein a front end flap comprises the front outer sheet that is folded over the front distal edge of the absorbent article to form a front waist flap region;

wherein the front waist flap region comprises a plurality of elastic strands and an elastomeric film, wherein the elastic strands overlap the elastomeric film;

wherein the back belt portion comprises a back inner sheet and a back outer sheet, wherein a back end flap comprises the back outer sheet that is folded over the back distal edge of the absorbent article to form a back waist flap region;

wherein the back waist flap region comprises a plurality of elastic strands and an elastomeric film, wherein the elastic strands overlap the elastomeric film; and wherein the elastomeric film in the front waist flap region and the plurality of elastic strands in the front waist flap region are separated by at least one of the front inner and outer sheets.

2. The article of claim 1, wherein at least the front waist end region and the back waist end region comprises a continuous waist graphic zone.

3. The article of claim 2, wherein the absorbent main body graphic zone comprises indicia comprising a plurality of graphic elements.

4. The article of claim 3, wherein the indicia comprises indication of the front and/or back side of the article.

5. The article of claim 4, wherein the indicia of the main body is non-directional.

6. The article of claim 1, wherein the back waist flap region has an opacity greater than the remainder of the back belt portion forming the back side panels.

7. The article of claim 3, wherein the main body graphic zone comprises a tummy graphic zone disposed on the front or back waist panel, and a leg graphic zone disposed adjacent the leg opening extending circumferentially about at least a portion of the leg opening.

8. The article of claim 7, wherein at least two selected from the group consisting of the waist graphic zone, leg graphic zone, and tummy graphic zone, are coordinated with one another to create a uniform graphical element.

9. The article of claim 7, wherein the front waist flap region has an opacity of at least 15 points greater than the remainder of the front belt portion forming the front side panels.

10. The article of claim 1, wherein the front and back belt portions each comprise an inner sheet, an outer sheet, and a plurality of elastic strands sandwiched between the inner and outer sheets, the elastic strands extending in the transverse direction to provide a continuous elastic ring when the front belt portion and the back belt portion are joined.

11. The article of claim 10, wherein the outer sheet of the front or back belt portion towards the distal end edge is longer than the size of the respective inner sheet in the longitudinal direction and an end flap of the outer sheet is folded over the distal end of the inner sheet to form the waist end region.

12. The article of claim 10, wherein the back waist flap region has an opacity equal to the front waist flap region.

13. The article of claim 1, wherein the plurality of elastic strands in the front waist flap region are disposed immediately adjacent to the front inner sheet.

14. The article of claim 1, wherein the elastomeric film in the front waist flap region is disposed between the front inner and outer sheets.

15. The article of claim 13, wherein the front waist end region comprises a waist graphic zone, wherein the waist graphic zone is disposed to overlap the elastomeric film.

16. The article of claim 11, wherein the end flap of the outersheet is further disposed in at least three layers.

17. The article of claim 10, wherein front belt portion and the back belt portion are rectangular.

18. The article of claim 6, wherein the waist flap region has an opacity of at least 15 points greater than the remainder of the belt portion forming the back side panels.

19. A process of manufacturing the article of claim 5, wherein the process is free of a step for registering the main body graphic zone relative to the direction or positioning of the absorbent main body.

20. The article of claim 1, wherein the plurality of elastic strands in the back waist flap region are disposed immediately adjacent to the back inner sheet.

21. The article of claim 1, wherein the elastomeric film in the back waist flap region is disposed between the back inner and outer sheets.

22. The article of claim 21, wherein the elastomeric film in the back waist flap region and the plurality of elastic strands in the back waist flap region are separated by at least one of the back inner and outer sheets.

23. The article of claim 20, wherein the back waist end region comprises a waist graphic zone, wherein the waist graphic zone is disposed to overlap the elastomeric film.

* * * * *